United States Patent [19]

Then et al.

[11] Patent Number: 5,919,669
[45] Date of Patent: *Jul. 6, 1999

[54] PROCESS FOR PREPARING L-TERTIARY-LEUCINE AND L-PHOSPHINOTHRICINE BY TRANSAMINATION

[75] Inventors: Johann Then, Hofheim am Taunus; Klaus Bartsch, Kelkheim; Hans-Matthias Deger, Hofheim am Taunus; Susanne Grabley, Königstein/Taunus; Rüdiger Marquardt, Frankfurt am Main, all of Germany

[73] Assignee: Hoechst Aktiengesellschaft, Frankfurt am Main, Germany

[*] Notice: This patent is subject to a terminal disclaimer.

[21] Appl. No.: 08/466,697

[22] Filed: Jun. 6, 1995

Related U.S. Application Data

[62] Division of application No. 08/411,072, Mar. 27, 1995, Pat. No. 5,753,470, which is a continuation of application No. 07/978,469, Nov. 19, 1992, abandoned, which is a continuation of application No. 07/520,955, May 9, 1990, abandoned, which is a continuation of application No. 07/056,715, Jun. 2, 1987, abandoned.

[30] Foreign Application Priority Data

Jun. 4, 1986 [DE] Germany .............................. 36 18 812

[51] Int. Cl.$^6$ ........................... C12P 13/04; C12N 15/74; C12N 15/78
[52] U.S. Cl. ...................... 435/106; 435/193; 435/252.3; 435/252.34
[58] Field of Search ................................ 435/106, 116, 435/193, 252.3, 252.34; 536/23.2

[56] References Cited

U.S. PATENT DOCUMENTS

| | | | |
|---|---|---|---|
| 3,660,235 | 5/1972 | Okumura et al. | 435/108 |
| 3,767,528 | 10/1973 | Nagasaki et al. | 435/108 |
| 4,518,692 | 5/1985 | Rozzell | 435/116 |
| 4,525,454 | 6/1985 | Rozzell | 435/106 |
| 4,542,069 | 9/1985 | Mauz et al. | 428/402 |
| 4,600,692 | 7/1986 | Wood et al. | 435/108 |
| 4,603,111 | 7/1986 | Keller et al. | 435/182 |
| 4,710,467 | 12/1987 | Wood et al. | 435/182 |
| 4,880,738 | 11/1989 | Rozzell et al. | 435/106 |
| 5,091,314 | 2/1992 | Marquardt et al. | 435/252.33 |
| 5,120,654 | 6/1992 | Marquardt et al. | 435/252.33 |
| 5,130,246 | 7/1992 | Schulz et al. | 435/193 |
| 5,316,943 | 5/1994 | Kidman et al. | 435/280 |
| 5,480,786 | 1/1996 | Kretzschmar et al. | 435/106 |

FOREIGN PATENT DOCUMENTS

| | | |
|---|---|---|
| 135846 | 4/1985 | European Pat. Off. . |
| 137372 | 4/1985 | European Pat. Off. . |
| 151488 | 8/1985 | European Pat. Off. . |
| 152275 | 8/1985 | European Pat. Off. . |
| 249188 | 12/1987 | European Pat. Off. . |
| 349965 | 1/1990 | European Pat. Off. . |
| 3237341 | 4/1984 | Germany . |
| 3243591 | 5/1984 | Germany . |
| 3423936 | 1/1986 | Germany . |
| 2152503 | 8/1985 | United Kingdom . |
| 2161159 | 1/1986 | United Kingdom . |

OTHER PUBLICATIONS

Chemical Abstracts, vol. 102, No. 147439h, 1985.
Lee–Peng et al., "Transaminase B from *Escherichia coli*: Quaternary Structure, Amino–Terminal Sequence, Substrate Specificity, and Absence of a Separate Valine–α–Ketoglutarate Activity," *Journal of Bacteriology*, vol. 139, No. 2, Aug. 1979, pp. 339–345.
Ziehr et al., "Isolation and Characterization of a Highly Inducible L–Asparate–phenylpyruvate Transaminase from Pseudomonas Putida," *Journal of Biotechnology*, vol. 3, 1985, pp. 19–31.
Fraser et al., "Kinetics for Glutamine–Synthetase Inhibition by Phosphinothricin and Measurement of Other Enzyme Activities In Situ in Isolated Asparagus Cells Using a Freeze–Thaw Technique," *Planta*, vol. 161, 1984, pp. 470–474.
Plaskie et al., "Substrate Specificity of Penicillin Acylase of E. Coli," *The Journal of Antibiotics*, vol. XXXI, No. 8, 1978, pp. 783–788.
Singleton et al., *Dictionary of Microbiology*, 1978, pp. 258 and 436.
Stan et al., *The Prokaryotes*, vol. II, 1984, pp. 1816–1819.
Tebbe et al., "Utilization of the Herbicide Phosphinothricin as a Nitrogen Source by Soil Bacteria," *Applied Microbiology and Biotechnology*, vol. 29, 1988, pp. 103–105.
ATCC Classifications of *Agrobacterium tumefaciens, Streptomyces hygroscopicus and Streptomyces viridochromogenes*, pp. 65, 215, and 229.
DSM Classification of *Escherichia coli* K 12 HB 101, p. 58.
Lehninger, *Principles of Biochemistry*, 1982, pp. 100–102.
E.L. Winnacker, From Genes to Clones: Introduction to Gene Technology, pp. 136, 137, 253, 256–259; German Edition (1985), pp. 190 and 298.
Lehninger, *Biochemistry*, 1975, pp. 73–75, 218, and 562.
Chemical Abstracts, vol. 93, No. 6148w, 1980.
Chemical Abstracts, vol. 97, No. 37513y, 1982.

*Primary Examiner*—Charles L. Patterson, Jr.
*Attorney, Agent, or Firm*—Finnegan, Henderson, Farabow, Garrett & Dunner, L.L.P.

[57] ABSTRACT

L-tertiary-Leucine and L-phosphinothricine are obtainable by transamination of the corresponding keto acids as a precursor in the presence of amino acids as amino group donors. The reaction is preferably carried out with microorganisms or their transaminases.

19 Claims, No Drawings

PROCESS FOR PREPARING L-TERTIARY-LEUCINE AND L-PHOSPHINOTHRICINE BY TRANSAMINATION

This is a divisional of Ser. No. 08/411,072, filed Mar. 27, 1995 now U.S. Pat. 5,753,470, which is a continuation of Ser. No. 07/978,469, filed Nov. 19, 1992, now abandoned, which is a continuation of Ser. No. 07/520,955, filed May 9, 1990, now abandoned, which is a continuation of Ser. No. 07/056,715, filed Jun. 2, 1987, now abandoned.

Optically active, non-proteinogenic amino acids have gained great importance because of their known or potential biological activities. Some are successfully used in the pharmaceutical sector, such as L-dihydroxyphenylalanine (L-dopa) or α-methyldopa, or are used in plant protection, such as phosphinothricine. Others are precursors of pharmaceuticals, such as D-phenylglycine or β-p-hydroxyphenylglycine in the preparation of the semisynthetic penicillins ampicillin and amoxycillin. They can also represent valuable intermediates for the synthesis of fine chemicals. Especially tertiary-leucine has also been adopted for the asymmetric synthesis of amino acid derivatives [U. Schöllkopf, Pure and Appl. Chem., 55 1799–1806, (1983)].

The non-proteinogenic optically active amino acids are preferably prepared only by a chemical method. A disadvantage in this case is that it is impossible to work stereoselectively and the end product obtained is the racemate. By contrast, enzymatic processes very frequently have the advantage that a chiral compound can be synthesized selectively from easily preparable intermediates by means of an enzyme step. This is a particular advantage if only one of the two stereoisomeric compounds is biologically active.

The synthesis of natural, so-called proteinogenic amino acids by biotransformation with a transaminase is known per se. European Patent Application 152,275 describes a process for the preparation of phenylalanine by transamination by means of a genetically modified microorganism which is distinguished by overproduction of aminotransferase. According to European Patent Application 135,846, natural L-amino acids are prepared by reacting α-keto acids with L-aspartic acid as the amino group donor in the presence of a transaminase which was isolated from E. coli. This gives the L-amino acids corresponding to the α-keto acid and oxalacetate from the aspartic acid.

The selection and mutation of microorganisms from the series E. coli, Paracoccus denitrificans, Torula, Rhodotorula and Streptomyces for the preparation of L-phenylalanine from phenylpyruvic acid in an improved yield are reported in German Patent Application 3,423,936.

Not naturally occurring, so-called non-proteinogenic amino acids have hitherto not been prepared by enzymatic biotransformation.

It has now been found that the synthesis of the non-proteinogenic amino acids L-tertiary-leucine and L-phosphinothricine can be carried out in a very good yield by means of transamination. This is surprising, inasmuch as it was admittedly known that various natural proteinogenic amino acids can be synthesized by means of transaminases, but that it was not to be expected because of the specificity of the enzymes that non-proteinogenic amino acids can likewise be prepared by this method using not naturally occurring α-keto acids as the precursor. It is therefore surprising that the corresponding precursors, in spite of their hydrophobic radicals not occurring in this form in the precursors for natural amino acids, are tolerated and converted by the active center of the transaminase.

The invention thus relates to a process for preparing L-tertiary-leucine and L-phosphinothricine, which comprises transaminating 3,3-dimethyl-2-oxo-butanoic acid and (3-carboxy-3-oxo-propyl)-methylphosphinic acid or in each case the corresponding salts in the presence of amino group donors.

The invention is explained in detail below and defined in the patent claims.

Enzymes from numerous organisms, for example from microorganisms, plants and animal organs, such as porcine heart, are capable of converting α-keto acids by transamination into natural L-amino acids. These organisms or their enzymes can be used according to the invention. Preferably, however, microorganisms are used which contain a transaminase, for example microorganisms of the genera Paracoccus, Alcaligenes, Rhizobium, Pseudomonas, Serratia, Agrobacterium, Streptomyces or enterobacteria. Microorganisms such as, for example, Alcaligenes faecalis DSM 4115, Alcaligenes denitrificans DSM 4114, Pseudomonas paucimobilis DSM 4120, Pseudomonas spec. DSM 4119, Serratia plymuthica DSM 4116, Agrobacterium tumefaciens, Escherichia coli DH1, Escherichia coli ATCC 11303, Enterobacter agglomerans DSM 4122, Enterobacter spec. DSM 4121, Paracoccus denitrificans DSM 65, Streptomyces hygroscopicus and Streptomyces viridochromogenes as well as 3 soil isolates DSM 4113, DSM 4117 and DSM 4118 are particularly advantageous.

These microorganisms were deposited at "Deutsche Sammlung für Mikro-organismen" und Zellkulturen GmbH, Mascheroder Weg 1B, D3300 Braunschweig, West Germany (DSM) on May 12, 1987, unless they were already freely available or described in such a manner as to enable the invention to be carried out by a person skilled in the art.

Higher enzyme activities can be obtained when strains are selected which are resistant to phosphinothricine or utilize phosphinothricine as the sole nitrogen source, for example Alcaligenes faecalis DSM 4115, Agrobacterium tumefaciens and the soil isolate DSM 4113. This is advantageous, but not absolutely necessary. Likewise, one can choose, by selection and mutation, in a manner known per se, against increasing amounts of 3,3-dimethyl-2-oxo-butanoic acid, phenylpyruvic acid or (3-carboxy-3-oxo-propyl)-methylphosphinic acid or salts thereof in the culture media, microorganisms for the further work which, due to their adaptation to the α-keto acid, effect the transamination in better yields. 3,3-Dimethyl-2-oxo-butanoic acid and salts thereof are readily accessible by saponification of trimethylacetic acid in the presence of thionyl chloride and KCN by conventional methods. The preparation of (3-carboxy-3-oxo-propyl)-methylphosphinic acid or salts thereof is likewise carried out by known methods (Hans Beyer, Lehrbuch der organischen Chemie [Textbook of Organic Chemistry], S. Hirzel Verlag, Stuttgart).

Good yields are also obtained when genetically manipulated microorganisms are used in the process according to the invention. E. coli ATCC 11303, which has been transformed with a plasmid containing a tyrB gene or ilvE gene, the tyrB gene coding for the aromatic transaminase and ilvE for the aliphatic transaminase in E. coli, is used with particular preference. Strains manipulated in this way can be prepared, for example, in accordance with German Patent Application P 36 31 829.9 or P 36 36 722.2.

The transamination can take place simultaneously with culturing, in which case microorganisms are then preferably used which are resistant to phosphinothricine, for example Alcaligenes faecalis DSM 4115 and Agrobacterium tumefaciens. However, the microorganisms are advantageously cultured in a nutrient medium which is optimum for their growth, under appropriate favorable temperature and aeration conditions up to a dry weight of about 4 to 60 g/l of nutrient solution. The most favorable conditions for the particular microorganisms are either known to a person skilled in the art or can be established by simple preliminary tests. The cells are then used, in the nutrient solution or separated from the nutrient solution, for aminating the α-keto acids. The transamination can be carried out with whole cells or with disrupted cells, the conventional disruption methods being used. It is also possible to carry out the transamination with cell extracts, isolated total proteins or purified transaminases. However, for practical considerations, for example cost reasons, intact cells are preferably used. Owing to a relatively long life of the enzyme and better controllability of the reaction, however, isolation of the transaminases can also be advantageous. In addition, it is possible to employ the microorganisms or the enzymes in an immobilized form. The known methods can be used for immobilization, advantageously the methods according to German Offenlegungsschriften 3,237,341 and 3,243,591.

In the preferred embodiment, the microorganisms or the isolated enzyme system are suspended in a physiological buffer, in such a way that their transaminase activity is not significantly affected in a negative way, the α-keto acid and the amino group donor being added. Depending on the quantity of the microorganisms, the enzymatic activity added to the batch in the form of microorganisms or the isolated enzyme system can vary within wide ranges. Advantageously, it is between 10 and 20,000 μmol/minute× liter. Preferably, the batch contains cell quantities with an enzyme activity of 1500–2000 μmol/minute×liter.

Amino acids are used as the amino group donor. The amino acid which is used with advantage depends largely on the microorganism or on the isolated enzyme system, but this can be established in short preliminary tests. Suitable examples are valine, leucine, isoleucine, methionine, tyrosine and phenylalanine, and especially asparagine, aspartic acid, glutamine, glutamic acid and glycine. These amino acids are used in the L-form, since only this compound is utilized according to the invention, as the free acid or as suitable salts (corresponding to the medium used). For the preparation of L-tertiary-leucine, 3,3-dimethyl-2-oxo-butanoic acid is used, whereas for the preparation of L-phosphinothricine (3-carboxy-3-oxo-propyl)-methylphosphinic acid is used as the α-keto acid. Salts thereof can also be used, the ions selected obviously being those which do not have a significant adverse effect on the transaminase activity. Preferably, these are Na, K and ammonium salts. The amino group donor is added in equimolar amounts or in excess to the α-keto acid. Ratios of 1:1 to 5:1, advantageously 1:1 to 2:1, have proven suitable.

The reactants can be added simultaneously to the reaction batch, as a solution in water or by adding the solid substances. However, a staggered or continuous addition in quantities of 0.1–4.5%, in particular 0.2–2%, each relative to the weight of the reaction batch, over a period of 1–90 hours, preferably 2–40 hours, is preferred.

Advantageously, the reaction is carried out at a pH between 5 and 9, especially between 7 and 8.5. In addition, it is expedient to carry out the transamination in a temperature range of 10°–65° C., especially 20 to 50° C. At lower temperatures, the enzyme reaction proceeds increasingly slowly, whereas the enzyme is progressively deactivated at higher temperatures.

The most advantageous procedure depends on the particular microorganism and can readily be established by simple preliminary tests.

It has proven to be particularly advantageous to permeabilize the microorganisms before or during the transamination reaction. This can be effected by addition of suitable agents, such as toluene, cetyltrimethylammonium bromide, dimethyl sulfoxide etc., to the incubation medium.

The examples which follow serve to illustrate the present invention in more detail. Unless otherwise stated, percentage data relate to the weight.

EXAMPLE 1

Culturing and working-up of the microorganisms

The bacteria as mentioned above, deposited or freely available, were cultured overnight in 400 ml liquid cultures in LB medium [Luria-Bertani medium: 10 g of Bacto Tryptone/5 g of Bacto yeast extract/10 g of NaCl per liter, (pH 7.5)] or M9 minimal medium [6 g of $Na_2HPO_4$/3 g of $KH_2PO_4$/0.5 g of NaCl/1 g of $NH_4Cl$/2 ml of 1 M $MgSO_4$+ 10 ml of 20% glucose+0.1 ml of 1 M $CaCl_2$+1 ml of 1% vitamin B1 (thiamine) per liter (pH 7.4)] at 30° C. (all bacteria except *E. coli*) or 37° C. (*E. coli*, DH1).

The bacteria were then centrifuged off and the cell pellets were washed repeatedly in 10 mM $Na_2HPO_4$, 10 mM NaCl (pH=7.0) (washing buffer) and finally suspended in 5 ml of washing buffer per 3 g of cell pellet. The cells were disrupted by 5 ultrasonic treatments of 1 minute each, and the cell fragments were then centrifuged off. The lysate supernatants thus obtained can be stored for several months at −20°0C.

EXAMPLE 2

Protein isolation

For protein isolation, 5 ml of the lysate supernatants were in each case made up to 50 ml with washing buffer and the proteins were precipitated by adding ammonium sulfate to 65%. After the protein pellets had been centrifuged in 15 minutes at 10,000 g, they were resuspended in each case in 5 ml of 10 mM $Na_2HPO_4$ (pH 7.0), 1 mM EDTA, 2% of glycerol and 1 mM dithiothreitol (DTT). This suspension can also be stored at −20° C. To achieve a better purification effect, some of the proteins were precipitated twice with ammonium sulfate.

The protein determinations were carried out by the biuret method. The protein content of the preparations carried out in accordance with the above instructions was in most cases between 5 and 10 mg/ml. For a partial purification of the transaminases from *Alcaligenes faecalis* DSM 4115 and from DSM 4113, the proteins were fractionally precipitated with 25% to 75% ammonium sulfate, in steps of 10% each, and the individual fractions were tested for transaminase activity (see below). The protein fractions of the highest specific activity were applied to a Sephadex G 100 gel filtration column and eluted with 10 mM $Na_2HPO_4$ (pH 7.0). The eluate fractions having the highest specific transaminase activity were concentrated by repeated ammonium sulfate precipitation and taken up to 5 mg/ml in 10 mM $Na_2HPO_4$ (pH 7.0), 1 mM EDTA, 2% glycerol and 1 mM DTT.

The molecular weights of the (®Sephadex G 100) poly-dextran column fractions were determined by comparison with molecular weight standard proteins. It was possible to check the purity of the isolated transaminase fractions by electrophoresis of protein samples in 10% SDS/polyacrylamide gels.

EXAMPLE 3

Phosphinothricine synthesis tests in liquid cultures 5 ml cultures of each of the bacteria strains were prepared in LB medium with 3 g/l (20 mM) L-glutamic acid on the sole N source and 2 g/l (10 mM) sodium (3-carboxy-3-oxo-propyl)-methylphosphinate at 30 ° C. 1 ml samples were taken after 1 and 2 days, and the bacterial cells were killed by heating to 95° C. for 20 minutes. After centrifugation, the supernatants were taken off and tested for phosphinothricine formation in an amino acid analyzer (AA analyzer). *Alcaligenes faecalis* DSM 4115 converts the substrates after 24 hours to 0.3 g/l L-phosphinothricine (15% conversion, relative to α-keto acid). After 48 hours, 5 g/l L-phosphinothricine are obtained (25% conversion).

EXAMPLE 4
Transaminase tests with cell extracts and protein isolates

Lysate supernatants and isolated total proteins of the bacteria as well as enriched transaminase fractions of *Alcaligenes faecalis* DSM 4115 and from DSM 4113 were adjusted with 10 mM $Na_2HPO_4$ and 10 mM NaCl (pH 7.0) to a protein content of between 20 and 60 mg/ml and incubated in a standard experiment with 80 mM L-glutamic acid as an $NH_2$ donor and 20 mM sodium (3-carboxy-3-oxo-propyl)-methylphosphinate at 30° C. Depending on the experimental conditions, 100 μl samples were taken between 0 and 24 hours' incubation time, the proteins were denatured for 10 minutes at 95° C. and centrifuged off, and the reaction supernatants were tested in the AA analyzer for phosphinothricine.

Control reactions did not contain any donor amino acid or sodium (3-carboxy-3-oxo-propyl)-methylphosphinate or were carried out with heat-inactivated proteins (10 minutes at 95° C.).

The formation of phosphinothricine was completely suppressed by addition of 10 mM hydroxylamine as a specific transaminase inhibitor.

The specific phosphinothricine transaminase activities were reported as nmol of phosphinothricine formed per mg of protein and per hour. The transamino reactivities were reported as μmol of phosphinothricine per minute and per mg of protein or per liter (U/mg of protein; U/L). 1 unit (U) corresponds to a conversion to give 1 μmol of L-phosphinothricine/minute.

| | | Yields of L-PTC (after 20 h reaction time): (Starting concentrations: 12 g/l L-glutamate, 4 g/l L-keto-PTC): | Conversion rates (after 20 h reaction time) |
|---|---|---|---|
| Strains | Enzyme activities: | | |
| a) L-Phosphinothricine (PTC) synthesis with lysate supernatants (unpurified) | | | |
| *Alcaligenes faecalis* DSM 4115 | 0.1 U/mg protein (2500 U/l) | 3.6 g/l | 90% |
| DSM 4113 | 0.04 U/mg protein (2000 U/l) | 3.8 g/l | 95% |
| *E. coli* (DH1) | 0.02 U/g protein (900 U/l) | 3.2 g/l | 80% |
| Strains | Enzyme activities: | L-PTC yields (see 4a) | Conversion rates (see 4a) |
| b) L-PTC synthesis with isolated total proteins (purified with $(NH_4)_2SO_4$) | | | |
| *Alcaligenes faecalis* DSM 4115 | 0.05 U/mg protein 1000 U/l | 3.8 g/l | 95% |
| *E. coli* (DH1) | 0.01 U/mg protein 500 U/l | 3.6 g/l | 90% |
| c) L-PTC synthesis with purified transaminase enzyme | | | |
| *Alcaligenes faecalis* DSM 4115 | 0.5 U/mg protein 10,000 U/l | 3.9 g/l | 97.5% |
| DSM 4113 | 0.2 U/mg protein 6000 U/l | 3.8 g/l | 95% |

EXAMPLE 5
Tests for stereoselectivity of the phosphinothricine synthesis

The stereospecificity of the formation of phosphinothricine by transamination was checked by means of the N-acetyl-transferase reaction. This enzyme was detected in a few soil bacteria (for example German Patent Application P 36 28 747.4) and can be isolated by known methods. It reacts stereospecifically only with L-phosphinothricine, which is quantitatively converted into the corresponding N-acetyl derivative by a reaction depending on acetyl-CoA.

In the test, reaction supernatants from Example 4, wherein phosphinothricine had been formed by transamination, were incubated for 5 hours at 30° C. with a protein from *Alcaligenes faecalis* DSM 4115 (to 1 mg/ml) and 10 mM acetyl -CoA. The reaction supernatants were then tested again in the AA analyzer for unconverted phosphinothricine.

The phosphinothricine formed enzymatically by transamination was completely degraded in each case by the N-acetyl-transferase reaction. This proves the stereoselectivity of the transamination. Pure L-phosphinothricine is formed.

EXAMPLE 6
Selection of *Escherichia coli* ATCC 11303

*Escherichia coli* ATCC 11303 was cultured by conventional methods and mutated with N-methyl-N-nitro-N-nitroguanidine (MNG) in accordance with E. Adelberg et. al., Biochem. Biophys. Res. Comm. 18, 788 (1965). The MNG-treated cells were streaked on an autoclaved agar of the following composition:

| | |
|---|---|
| Fumaric acid | 5 g/l |
| Meat extract | 20 g/l |
| Aspartic acid | 20 g/l |
| KH$_2$PO$_4$ | 2 g/l |
| MgSO$_4$.7H$_2$O | 0.5 g/l |
| CaCl$_2$.2H$_2$O | 0.1 g/l |
| Agar | 20 g/l |

The pH was adjusted to 7.2 with sodium hydroxide solution.

A sterile-filtered solution of phenylpyruvate was poured into the agar while still hot, in such a way that a final concentration of 24 g/l phenylpyruvate was reached. The plates were incubated for 4 days at 37° C. Colonies of a diameter of >1 mm were isolated. 20% of the growing strains had a transaminase activity which was higher than that of the starting strain.

The determination of transaminase activity was carried out by means of the Sigma test kit G 0390.

EXAMPLE 7 a. Isolation and digestion of the cosmid pIMS 6026 from E. coli

The cosmid pIMS 6026 is derived from the cosmid pLAFRI (ATCC 37167) by cloning into its unique EcoRI cleavage site the commercially available EcoRI fragment on which the kanamycin-resistance gene of the transposon Tn 903 is located (Pharmacia, Uppsala, Sweden). By digestion with BamHI and subsequent religation, the major part of the commercially available EcoRI fragment can be deleted, so that only a short piece of DNA remains as an insertion, in which a BamHI cleavage site is flanked by 2 EcoRI cleavage sites.

To isolate the cosmid pIMS 6026 from *E. coli* HB101, either the procedure of Humphreys et al. [Biochim. Biophys. Acta 383, 457–63 (1975)] or an alkaline lysis according to Birnboim and Doly [Nucteic Acids Res. 7, 1513 (1979)] was carried out on a 10 times larger scale. In each case, the plasmid DNA was purified at least once by CsCl/EtBr density gradient centrifugation.

The cosmid pIMS 6026 was completely digested by the restriction enzyme BamHI, following the instructions of the manufacturer, New England Biolabs. To check the completeness of this digestion, an aliquot of the restriction preparation was applied to a 0.8% agarose gel and subjected to electrophoresis. The appearance of only one band after staining with ethidium bromide and irradiation with short-wave UV light (254 nm) was taken as an indication of complete digestion. The restriction enzyme was removed from the digested cosmid DNA by phenol treatment, and the DNA was precipitated by means of ethanol, washed with 70% ethanol and, after drying in vacuo, taken up in a suitable volume of TE buffer (10 mM tris; 1 mM EDTA, pH 8.0). In selected cases, a treatment with alkaline phosphatase in accordance with the instructions of the manufacturer, Boehringer Mannheim, was also carried out. After an addition of 1 μl of alkaline phosphatase (CIP) incubation was carried out for 30 minutes at 37° C., the enzyme was removed from the reaction mixture by phenol treatment, and the DNA was purified as described above. Finally, it was resuspended in TE buffer.

b. Partial digestion of DNA from *E. coli* ATCC 11303.

The isolation of the total DNA from *E. coli* ATCC 11303 was carried out by the method of Marmur in J. Mol. Biol. 53, 155–162, (1961). The isolated total DNA was partially digested by the restriction enzyme Sau3A, so that mainly fragments in the size range 20–30 kb were formed. To do this, the optimum DNA/enzyme ratio for this purpose and the optimum time of action of the enzyme on the DNA was determined in preliminary experiments. The appropriate procedure is described on page 3 of the pamphlet "focus", Vol. 7, No. 2 (1985), issued by BRL. After the reaction time determined as being the optimum had elapsed, the enzyme was destroyed by heating to 65° C. for a period of 10 minutes, and the formation of DNA fragments in the desired range of sizes was checked by agarose gel electrophoresis with suitable DNA markers, for example with EcoRI-digested DNA of phage λ.

c. Ligation of the restriction sites

Total DNA, partially digested with Sau3A, from *E. coli* ATCC 11303 was combined in a molar ratio of approximately 1:5 with pIMS 6026 cosmid DNA which had been completely cleaved with BamHI and treated with alkaline phosphatase. The resulting mixture was treated with a several-fold concentrated buffer in accordance with the New England Biolabs instructions in such a way that an optimum ion concentration for the enzyme T4 DNA ligase was obtained, and incubated for at least 14 hours at 16° C. with 1 μl of the enzyme. The total volume of the mixture was 50 μl, with a total DNA concentration of 20 μg/ml.

d. Packaging in λ phages

After the ligase reaction had taken place, the DNA obtained according to Example 3 was packaged in vitro into the heads of λ phages. The extracts required for this purpose can be prepared from two different bacteria strains by the method of B. Hohn, in R. Wu, editor: Recombinant DNA, Methods in Enzymology, Vol. 68, Academic Press, New York, pages 299–309 (1979), or obtained from Boehringer Mannheim or Amersham Buchler, Brunswick.

3 μl of the mixture obtained according to Example 3 were thoroughly mixed, while cooling with ice, with bacteria extracts from Amersham which had been thawed just before. The mixture was incubated for 30–60 minutes at 20° C., and 200 μl of SM buffer (100 mM NaCl, 10 mM MgSO$_4$, 50 mM tris-HCl (pH 7.5) and 0.01% of gelatins) were then added. This mixture was either used directly for a transduction reaction or, after addition of 10 μl of chloroform, stored at 4° C. for later use.

e. Transduction of *E. coli* DG 30

0.4% of maltose was added to 5 ml of L broth, consisting of 1% of Bacto Tryptone, 0.5% of yeast extract and 0.5% of NaCl, and the mixture was inoculated with 50 μl of a liquid culture of *E. coli* DG 30 in the stationary phase of growth. The mixture was incubated for 12 hours at 37° C., until the early stationary phase had been reached. The bacteria were centrifuged off and carefully resuspended in 2.5 ml of an aqueous 10 mmolar MgCl$_2$ solution. 10 μl of the mixture according to example 4 were treated with 20 μl of the concentrated bacteria suspension and incubated for 50 minutes at room temperature.

200 μl of L broth were then added, and the mixture was incubated for 1 hour at 37° C. with occasional shaking.

50 μl of the preparation were in each case plated on L broth agar which contained 20 μg/ml tetracycline.

The plates were incubated for at least 12 hours at 37° C. Using the procedure described, it was possible to obtain 1000 colonies on average from one preparation.

f. Selection of *E. coli* DG 30 with an aspC or ilvE or tyrB gene.

About 800 colonies which had been obtained after transduction of *E. coli* DG 30 by the method described on L broth agar containing 20 μg/ml of tetracycline were "picked" onto minimal agar. The minimal agar consisted of M9 medium with glucose (Miller, Experiments in Molecular Genetics, Cold Spring Harbor, 1972), which had been supplemented by the amino acids isoleucine, leucine, valine, aspartic acid and phenylalanine. However, the amino acid tyrosine, which the DG 30 strain is likewise no longer able to synthesize, was not added to the medium. 7 of the 800 "picked" colonies were able to grow on the minimal medium.

To distinguish between the three possible genes aspC, ilvE and tyrB in *E. coli* DG 30, these 7 colonies were in turn "picked" onto the above mentioned minimal medium which had been supplemented with the amino acids listed, with the exception of one amino acid in each case, for which one of the transaminases coded for by one of the genes shows substrate specificity.

The result is shown in the table which follows:

Minimal medium, supplemented with the exception of presumed substrate

| Clone | Asp | Leu | Ile | Tyr | Gene |
|---|---|---|---|---|---|
| 1 | + | + | − | + | tyrB |
| 2 | + | + | − | + | tyrB |
| 3 | − | +− | + | +− | ilvE |
| 4 | − | +− | + | +− | ilvE |
| 5 | + | + | − | + | tyrB |
| 6 | + | + | − | + | tyrB |
| 7 | − | +− | + | +− | ilvE |

+ = good growth
+− = poor growth
− = no growth g. Localization of the tyrB gene

Cosmid DNA from clones 1 to 7, obtained according to Example 6, was prepared by minilysis according to Maniatis et al., Cold Spring Harbor, pages 366–370 (1982). This cosmid DNA was then introduced into *E. coli* DH1 (ATCC 33849), from which it could be reisolated in good yields.

Plasmid DNA, originally obtained from the clone 3 of *E. coli* DG 30 (see Example 6), was isolated from the *E. coli* DH1 strain transformed with this DNA and completely digested by the restriction enzymes SaiI and SmaI, following the instructions of the manufacturer, New England Biolabs. The vector pAT 153 was also completely digested by ClaI and then subjected to a further treatment with alkaline phosphatase. The two DNAs were combined, ligated with one another in the manner already described in Example 4, and competent cells of *E. coli* ATCC 11303 strain were transformed with an aliquot of the ligase preparation, for example 10 μl. Resistant colonies were selected on L broth plates containing 50 μg/ml ampicillin and tested by replica plating on L broth plates with 20 μg/ml tetracycline for marker inactivation and hence incorporation. Plasmid DNA was isolated by minilysis from colonies showing the AprTcs phenotype and the presence of ClaI fragments in the vector pAT153 was checked by complete digestion with the restriction enzyme ClaI.

h. Checking of the transaminase activity

The clones obtained according to Example 7 were tested by means of the APPAT test (aspartate-phenylpyruvate aminotransferase assay, Sigma test kit G0390, α-ketoglutarate being replaced by phenylpyruvate) for the activity of the aromatic transaminase, that is to say the gene product of tyrB. The non-transformed starting strain *E. coli* ATCC 11303 was used as a comparison. In one case, a marked increase in tyrB activity, namely by a factor of 5 to 10, as compared with the starting strain *E. coli* ATCC 11303 was measured.

By means of agarose gel electrophoresis using suitable markers, it was possible to show that the strain showing increased tyrB gene activity contained a pAT 153 vector which contained an incorporated ClaI fragment of size about 2.7 MD. When the plasmid-free strain *E. coli* ATCC 11303 was again transformed with the isolated plasmid DNA, an increase in the tyrB gene activity by a factor of 5–10 was observed in every case.

The transformation of *E. coli* ATCC 11303 with the ilvE gene is carried out in analogous manner.

EXAMPLE 8

Preparation of L-tertiary leucine a. An *Escherichia coli* ATCC 11303 strain selected according to Example 6 was cultured in the following nutrient solution:

| | |
|---|---|
| Fumaric acid | 10 g/l |
| Meat extract | 20 g/l |
| Aspartic acid | 8 g/l |
| KH$_2$PO$_4$ | 2 g/l |
| MgSO$_4$.7H$_2$O | 0.5 g/l |
| CaCl$_2$.2H$_2$O | 0.1 g/l |
| 3,3-Dimethyl-2-oxo-butanoic acid | 4 g/l |

The pH was adjusted to 7.4 with sodium hyroxide solution.

After 48 hours' growth at 37° C., the cells were centrifuged off. 0.9 g/l L-2-amino-3,3-dimethyl-butanoic acid (tertiary-leucine) was found in the supernatant by means of HPLC on an RPC 8 column (mobile phase: gradient of 100 mM Na acetate (pH 7.2) and methanol.

b. Cell material was cultured as in Example 8a and incubated with shaking in a solution of 10 g/l aspartic acid and 4 g/l 3,3-dimethyl-2-oxo-butanoic acid in 10 mmol/l tris HCl buffer (pH 7.4). After 24 hours at 37° C., 1.9 g/l L-2-amino-3,3-dimethyl-butanoic acid were measured by means of HPLC.

EXAMPLE 9

Preparation of L-phosphinothricine

Cell material was cultured as in Example 8 but with 4 g/l dimethylpyruvate in place of 3,3-dimethyl-2-oxo-butanoic acid. After 48 hours, the cells were centrifuged off, washed with buffer and incubated for 24 hours at 37° C. in an aqueous solution of 4 g/l sodium (3-carboxy-3-oxo-propyl)-methylphosphinate and 8 g/l sodium aspartate in 10 mmol/l tris/HCl (pH 7.4). The cells were then centrifuged off and the quantity of L-phosphinothricine formed was determined in the supernatant by HPLC analysis. 3.2 g/l phosphinothricine were found.

EXAMPLE 10

Preparation of L-phosphinothricine using recombinant bacteria

10 An *E. coli* strain from Example 7 with plasmid-coded ilvE transaminase activity was fermented in the following nutrient solution:

| | |
|---|---|
| glucose | 5 g/l |
| Na$_2$HPO$_4$ | 3.5 g/l |
| KH$_2$PO$_4$ | 1.8 g/l |
| (NH$_4$)$_2$HPO$_4$ | 12 g/l |
| (NH$_4$)$_2$SO$_4$ | 6 g/l |
| MgSO$_4$ | 0.2 g/l |
| Yeast extract | 1 g/l |

The pH was adjusted to 7.0 with NaOH.

After 4 hours' growth, an exponential glucose supplementation between 0.5 and 20 g/l/h was started. After 16 hours' growth, the cells had a dry weight of 20 g/l and a transaminase activity of 15,000 μmol/min/l. After the fermentation, the cells were used directly in a 100 ml reaction batch, without further washing steps. The reaction batch contains 1500 μmol/min/l transaminase activity, 0.1 ml of polyoxyethylene sorbitan monooleate (®Tween 80), 90 mmol/l sodium (3-carboxy-3-oxo-propyl)-methylphosphinate and 200 mmol/l glutamic acid in a 10 mmol/l tris-HCl buffer (pH 7.4), and it was gently shaken at 37° C. After 24 hours, the cells were centrifuged off and L-phosphinothricine was determined in the supernatant by HPLC analysis. 70 mmol/l L-phosphinothricine were found.

We claim:

1. A process for preparing L-phosphinothricine, which comprises incubating an α-keto acid selected from (3-carboxy-3-oxo-propyl)-methylphosphinic acid and a salt of (3-carboxy-3-oxo-propyl)-methylphosphinic acid in the presence of:
  (i) an L-amino acid as an amino group donor, and
  (ii) a microorganism which transaminates the α-keto acid, or transaminase enzyme of said microorganism, wherein:
    (A) said microorganism is selected from the genera Paracoccus, Alcaligenes, Pseudomonas, Serratia, Agrobacterium, Streptomyces, Escherichia, or Enterobacter, or is a soil isolate selected from the group consisting of soil isolate DSM 4113, soil isolate DSM 4117, and soil isolate DSM 4118; and
    (B) the genome of said microorganism contains a transformed or mutated gene such that said microorganism's ability to transaminate said α-keto acid is enhanced, wherein
      said transformed or mutated gene is derived from said genera or said soil isolate.

2. The process as claimed in claim 1, wherein said microorganism is selected from the group consisting of *Alcaligenes faecalis* DSM 4115, *Alcaligenes dentrificans* DSM 4114, *Pseudomonas paucimobilis* DSM 4120, Pseudomonas spec. 4119, *Serratia plymuthica* DSM 4116, *Agrobacterium tumefaciens, Escherichia coli* DH1, *Escherichia coli* ATCC 11303, *Enterobacter agglomerans* DSM 4122, Enterobacter spec. DSM 4121, *Paracoccus dentrificans* DSM 65, *Streptomyces hydrogscopicus*, and *Streptomyces viridochromogenes*.

3. The process as claimed in claim 1, wherein said microorganism has been transformed with a plasmid containing an *Escherichia coli* ATCC 11303 tyrB gene or an *Escherichia coli* ATCC 11303 ilvE gene.

4. The process as claimed in claim 3, wherein said microorganism is *Escherichia coil* ATCC 11303.

5. The process as claimed in claim 1, wherein the transamination is carried out using cell extracts, isolated total proteins, or purified transaminase.

6. The process as claimed in claim 1, wherein the amino group donor and the α-keto acid are employed at a ratio of 1:1 to 5:1.

7. The process as claimed in claim 6, wherein said ratio is from 1:1 to 2:1.

8. The process as claimed in claim 1, wherein the incubation is carried out at a pH in the range from 5 to 9.

9. The process as claimed in claim 8, wherein said pH is in the range from 7 to 8.5.

10. A process for preparing L-tertiary-leucine, which comprises incubating an α-keto acid selected from 3,3-dimethyl-2-oxo-butanoic acid and a salt of 3,3-dimethyl-2-oxo-butanoic acid, in the presence of:
  (i) an L-amino acid as an amino group donor, and
  (ii) a microorganism which transaminates the α-keto acid, or transaminase enzyme of said microorganism, wherein:
    (A) said microorganism is selected from the genera Paracoccus, Alcaligenes, Pseudomonas, Serratia, Agrobacterium, Streptomyces, Escherichia, or Enterobacter, or is a soil isolate selected from the group consisting of soil isolate DSM 4113, soil isolate DSM 4117, and soil isolate DSM 4118;
    (B) the genome of said microorganism contains a transformed or mutated gene such that said microorganism's ability to transaminate said α-keto acid is enhanced, wherein
      said transformed or mutated gene is derived from said genera or said soil isolate.

11. The process as claimed in claim 10, wherein said microorganism is selected from the group consisting of *Alcaligenes faecalis* DSM 4115, *Alcaligenes dentrificans* DSM 4114, *Pseudomonas paucimobilis* DSM 4120, Pseudomonas spec. 4119, *Serratia plymuthica* DSM 4116, *Agrobacterium tumefaciens, Escherichia coli* DH 1, *Escherichia coli* ATCC 11303, *Enterobacter agglomerans* DSM 4122, Enterobacter spec. DSM 4121, *Paracoccus dentrificans* DSM 65, *Streptomyces hydrogscopicus*, and *Streptomyces viridochromogenes*.

12. The process as claimed in claim 10, wherein said microorganism has been transformed with a plasmid containing an *Escherichia coli* ATCC 11303 tyrB gene or an *Escherichia coli* ATCC 11303 ilvE gene.

13. The process as claimed in claim 12, wherein said microorganism is *Escherichia coli* ATCC 11303.

14. The process as claimed in claim 10, wherein the transamination is carried out using cell extracts, isolated total proteins, or purified transaminase.

15. The process as claimed in claim 10, wherein the amino group donor and the α-keto acid are employed at a ratio of 1:1 to 5:1.

16. The process as claimed in claim 15, wherein said ratio is from 1:1 to 2:1.

17. The process as claimed in claim 10, wherein the incubation is carried out at a pH in the range from 5 to 9.

18. The process as claimed in claim 17, wherein said pH is in the range from 7 to 8.5.

19. A microorganism which contains a transformed or mutated gene, and which transaminates 3,3-dimethyl-2-oxo-butanoic acid, (3-carboxy-3-oxo-propyl)-methylphosphinic acid, or salts of these compounds in the presence of amino acids, wherein said microorganism is selected from the group consisting of *Alcaligenes faecalis* DSM 4115, *Alcaligenes dentrificans* DSM 4114, *Pseudomonas paucimobilis* DSM 4120, *Serratia plymuthica* DSM 4116, *Enterobacter agglomerans* DSM 4122, Enterobacter spec. DSM 4121, soil isolate DSM 4113, soil isolate DSM 4117, and soil isolate 4118, and said transformed or mutated gene is derived from the genera Paracoccus, Alcaligenes, Pseudomonas, Serratia, Agrobacterium, Streptomyces, Escherichia or Enterobacter.

* * * * *